United States Patent [19]

Plouff

[11] Patent Number: 4,878,899

[45] Date of Patent: Nov. 7, 1989

[54] DISPOSABLE SYRINGE FOR ONE-TIME USE

[76] Inventor: Frederick L. Plouff, 21A Sweetser St., Wakefield, Mass. 01880

[21] Appl. No.: 160,712

[22] Filed: Feb. 26, 1988

[51] Int. Cl.[4] ............................................. A61M 5/00
[52] U.S. Cl. .................................... 604/110; 604/218
[58] Field of Search ................ 604/110, 187, 218, 220

[56] References Cited

U.S. PATENT DOCUMENTS

| 4,731,068 | 3/1988 | Hesse | 604/110 |
| 4,781,684 | 11/1988 | Trenner | 604/110 |

FOREIGN PATENT DOCUMENTS 2184657  7/1987  United Kingdom ................ 604/110

*Primary Examiner*—John D. Yasko
*Attorney, Agent, or Firm*—Pearson & Pearson

[57] ABSTRACT

The disposable syringe comprises a cylindrical barrel having a side wall, an axis, and two ends, one of which, the distal end, has an inlet-outlet end for the administration of fluids. A cylindrical plunger is mounted snugly and fluid tight for axial movement within the barrel. An actuating rod has one, distal end connected to the plunger. The barrel at its other, proximal end has means for guiding the actuating rod axially. One or more pins of spring material are within the barrel, one, proximal end imbedded in the barrel side wall, and the other, free distal end located nearer the distal end of the barrel then the location of the proximal end of the pin. The plunger is movable from a position nearer the proximal barrel end to a position nearer the other, distal barrel end beyond the distal end of the pin, the barrel head on such movement camming the pin head outward from its normal position toward the wall of the barrel until the free end is freed by elasticity of the pin to return to its normal position radially within the wall, whereby on such movement the head is captured by the interposed pin free end to prevent return movement of the head toward the proximal end of the barrel thereby to prevent re-use of the syringe.

18 Claims, 3 Drawing Sheets

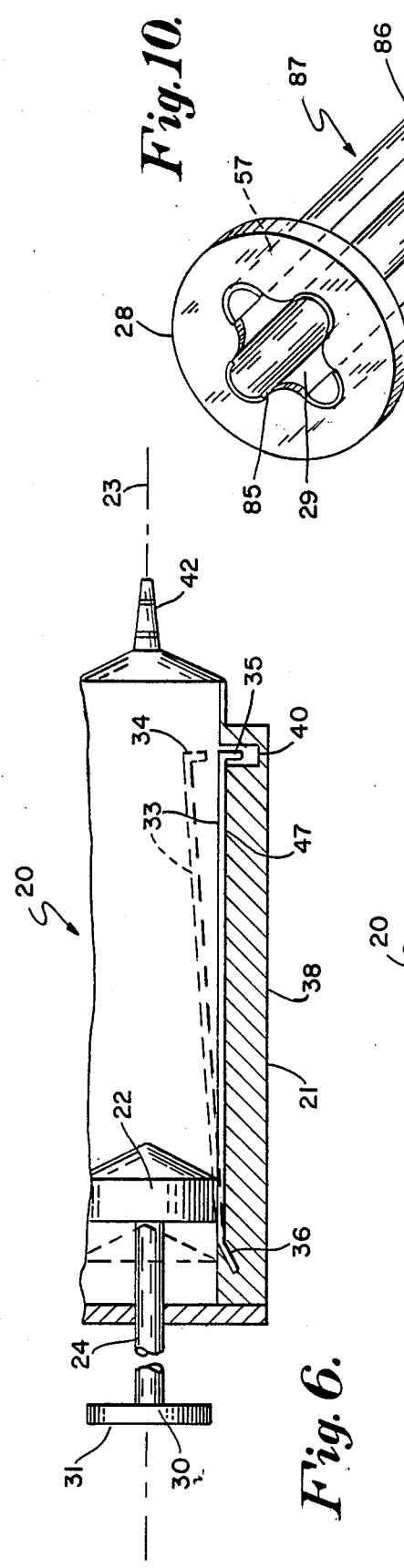

DISPOSABLE SYRINGE FOR ONE-TIME USE

FIELD OF THE INVENTION

The invention relates to disposable syringes which are intended for one-time use.

BACKGROUND OF THE INVENTION

Many efforts have been made to provide disposable syringes intended for one-time use. For example: U.S. Pat. No. 3,478,937 to Solowey Nov. 18, 1969, for Disposable Single Unit-dose Syringe with Locking Plunger has pawls 41 pivoted into notches 44 by force of the edge of the rigid collar 46 and after passing through the collar, the pawls spring outward to prevent upward movement of the plunger.

U.S. Pat. No. 3,890,971 to Leeson et al. June 24, 1975 for Safety Syringe describes a detent 19 having an upwardly inclined groove locking face 18b in order to prevent downward movement of the plunger after initial use.

U.S. Pat. No. 4,233,975 to Yerman Nov. 18, 1980 for Anti-drug Abuse Single-use Syringe describes a terminal end blocking flow through outlet 17 when female members 25 flexibly and resiliently snap back into locking position blocking flow into or from needle 22.

U.S. Pat. No. 4,252,118 to Richard et al. for Nonreusable Drug Prefilled Syringe Assembly and Method of Use describes a stopper and rod which become disconnected from each other after an injection is given and the plunger rod is withdrawn inside the barrel.

U.S. patent to Legendre et al. Jan. 11, 1983 for Prefilled Syringe for Abusable Drugs describes a spike 14 on a plunger rod 13 which prevent the rod from being withdrawn backward through the restricted opening.

U.S. Pat. No. 4,391,272 to Staempfli July 5, 1983, for Disposable Syringe describes a rim 7 of a plunger 6 which is blocked against the body 11 of the groove 5 which prevents the rearward return movement of the piston body 3.

U.S. Pat. No. 4,391,273 to Chiquiar-Arias July 5, 1983, for Non-reusable Disposable Syringes describes a sharp point of pin 67 which penetrates the bottom wall of the cylinder when the plunger is pressed home, making the syringe useless thereafter.

U.S. Pat. No. 4,493,703 to Butterfield Jan. 15, 1985 for Hypodermic Syringe Cartridge with Non-retractable Drive Piston which describes an actuator rod which disengages from an insert 18 when the rod is pulled away from the piston.

U.S. Pat. No. 4,650,468 to Jennings, Jr. Mar. 17, 1987 for Retractable Disposable Syringe describes various locking arrangements in which the cannula is withdrawn into the cylindrical body and securely locked within it.

SUMMARY OF THE INVENTION

According to the invention the disposable syringe for one-time use comprises a cylindrical barrel having an inlet-outlet end, a cylindrical plunger mounted fluid tight for axial movement in the barrel, an actuating rod for the plunger and having one end connected to the plunger, and the barrel having at the other barrel end means for guiding the rod axially. A pin within the barrel has two ends, one end fixed to the side wall of the barrel, and the other end free. When the plunger is moved toward the one end it cams the pin and its free end aside, and after it passes the pin, the pin returns to normal position and captures the plunger by interposing its free end to prevent return movement of the plunger. Thus the re-use of the syringe is prevented. The invention also involves a variety of other novel features.

DESCRIPTION OF THE DRAWING

The various objects, advantages, and novel features of the invention will be more fully apparent from the following detailed description when read in connection with the accompanying drawing, in which like reference characters refer to like parts, and in which:

FIG. 6 is a partial schematic view of still another embodiment of the invention;

FIG. 7 is a partial schematic view of still another embodiment of the invention;

FIG. 8 is a schematic view of a different embodiment of the invention;

FIG. 9 is a sectional view of the embodiment of FIG. 8 along the lines 9—9 of FIG. 8;

FIG. 10 is a perspective view of a modified cap of the embodiment of FIG. 8;

FIG. 10A is a side view of the plunger alone;

DETAILED DESCRIPTION

Figure 1:
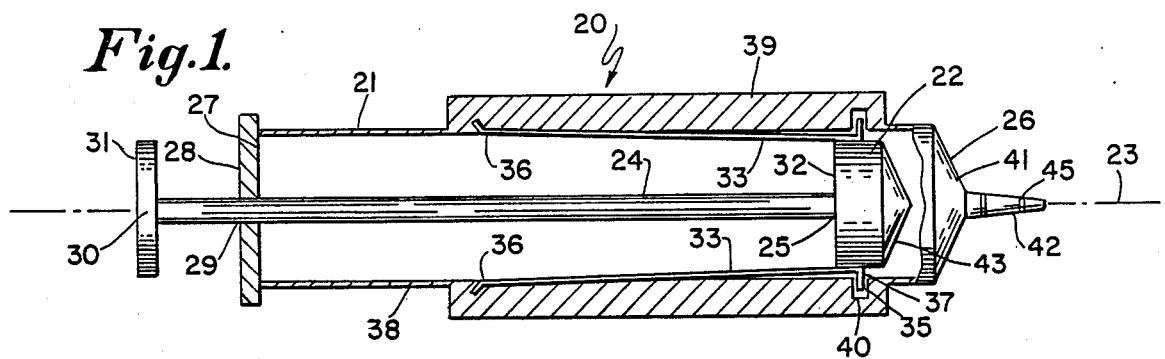
FIG. 1 is a schematic view of an embodiment of the invention.

A syringe 20 has a barrel 21 a plunger 22 which is fitted snugly and fluid tight within the barrel 21 to move axially along the direction of the axis 23. One end 25, the distal end, of the actuating rod 24 is connected to the plunger 22 to move the plunger toward one end 26, the distal end of the barrel 21 or toward the other, proximal end 27. The plunger 22 has a proximal face 32. The rod is guided by means of a cap 28 and a guiding aperture 29 in the cap capping the other, proximal end 27 of the barrel. The rod 24 has its other, proximal end 30 connected to a hand or finger grip 31.

Figure 2:
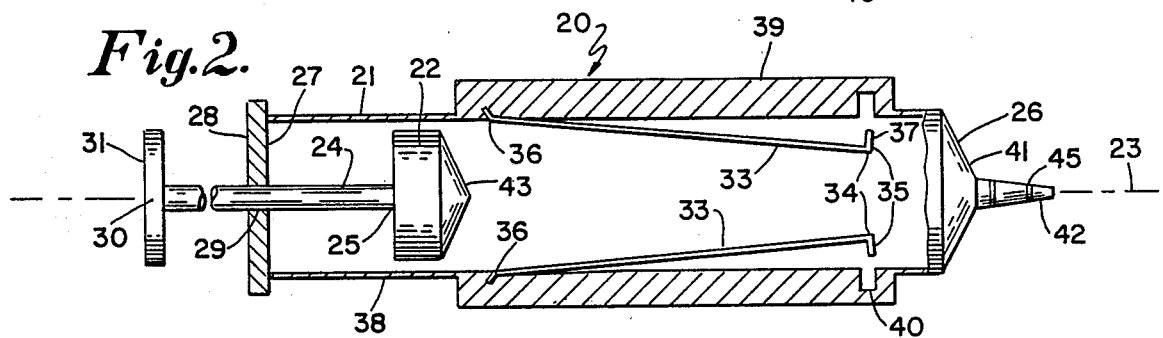
FIG. 2 is a schematic view of the embodiment of FIG. 1 with the plunger in retracted position.
Figure 3:
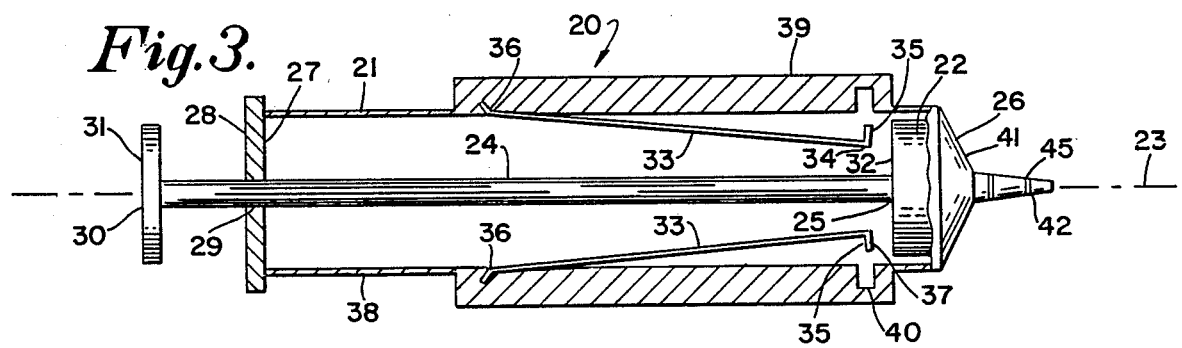
FIG. 3 is a schematic view of FIG. 1 with the plunger in fully extended position.

One or more pins 33 are shown in FIGS. 1-3, all alike and disposed at equal angular intervals about the axis 23. Description of one will serve for all. The pin 33 has at one, distal end 34 a bend or snub 35 having a surface 37 facing axially. The pins 33 are made of a spring material so that they will yield to radial forces and spring back. The other, proximal end 36 of the pins 33 are imbedded in the side wall 38 of the barrel 21. The side wall 38 of the barrel 21 is enlarged circumferentially as at 39 to strengthen the barrel about the other, proximal end 36 of the pins 33. The proximal end 36 of the pin 33 is imbedded in the side wall 38 and particularly in the enlarged portion 39. A small cell or pocket 40 is designed to receive the snub 35 of the free, distal end 34 when the pin 33 is pressed against the wall 38, as shown in FIG. 1.

In the front or forward direction of the syringe 20, the barrel terminates in a frusto-conical section 41 which is extended to a smaller angle conical nozzle 42 in the proximal direction designed to receive the proximal end of a needle (not shown) for administration of an injection. The nozzle has at least one raised rib 45 which seats in a rib receiving indent in the cap of a needle for various sizes of needles not shown. The distal face 43 of the plunger 22 is shaped conically to substantially match complementarily the frustoconical section 41 so that virtually all of the solution may be expressed in the administration of an injection.

In operation the syringe 20 is prepared at the factory with the plunger 22 only slightly withdrawn from the section 41. At this point the plunger 22 holds the pins 33 against the side wall 38 of the barrel 21. The solution to be administered may now be drawn into the barrel 21 by withdrawing the plunger using the rod 24 to position the plunger 22 to a position as shown in FIG. 2. After the needle (not shown) is fitted to the nozzle 42, and any extra air or gas expelled, the solution may be administered using grip 31 to force the rod to the distal end of its stroke, as shown in FIG. 3. As the plunger 22 passes down the barrel 21 from or near its most proximal position as shown in FIG. 2 towards the distal end, the plunger cams the pins 33 toward the side wall 38, and eventually the snubs 35 enter the pockets 40. When the proximal end of the plunger 22 passes the free, distal ends 34 of the pins 33 the pins are released axially, and the free distal ends 34 spring back to their normal position as indicated in FIGS. 2 or 3. If an attempt is made to withdraw the plunger proximally as best shown in FIG. 3, the free ends 34 and the surface 37 of the snubs 35 are interposed against the proximal face 32 of the plunger 22, preventing its return proximally. Therefore the syringe 20 may be used only once, and is now disposable.

The pins 33 may be employed without the snubs 35. Nevertheless the snubs 35 are useful in providing a more sure interposition against the withdrawal of the plunger 22 after use. The pockets 40 afford a way of storing the snubs 35 out of the way as the pins 33 are cammed aside by the distal stroke of the plunger 22.

Figure 4:
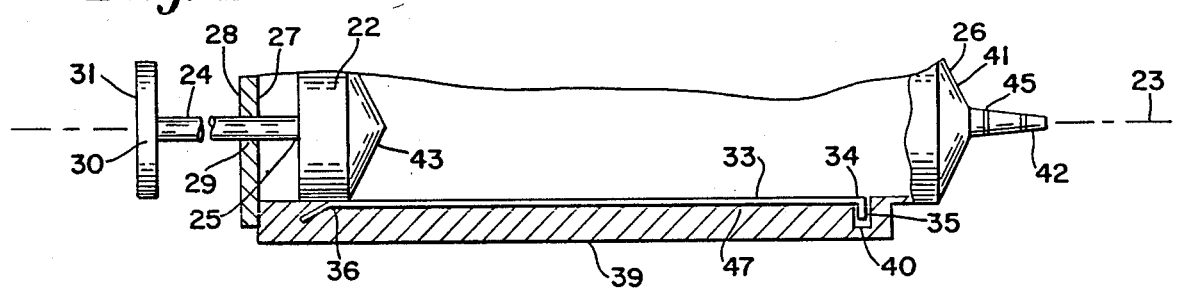
FIG. 4 is a partial schematic view of another embodiment of the invention with the plunger in retracted position.
Figure 5:
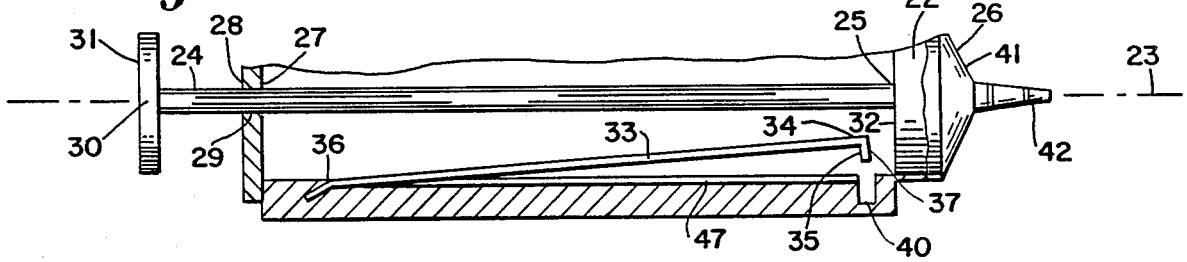
FIG. 5 is a partial schematic view of another embodiment of the invention with the plunger in a fully extended position.

In FIGS. 4 and 5, an arrangement similar to that of FIGS. 1–3 is illustrated, except that in the arrangement of FIGS. 4 and 5 an open groove 47 permits the pin 33 to rest therein throughout the length of the groove, and the pocket 40 is provided at the distal end of the groove. Nevertheless the imbedding of the pin 33 at its proximal end 36 may be modified sufficiently to assure that the free, distal end 34 of the pin 33 is carried well out into the barrel 21 spaced inwardly from the side wall 38 as indicated in FIG. 5.

In FIGS. 6 and 7, the imbedded end 36 of the pin 33 is distally located at the farthest position proximally that may be reached by the plunger 22. This arrangement assures that the piston always holds the pins 33 retained in the grooves 47, until the plunger makes a full stroke and reaches proximally to free the free, distal end 34 of the pins 33. Then the pins spring into their free position, indicated in dotted lines in FIG. 6.

FIG. 7 is similar to the arrangement of FIGS. 4 and 5, except that a compression spring 49 within the pocket 40 insures positively a return of the spring 33 to its normal position outside the groove 47 when the plunger 22 passes by the pin 33 proximally. In this case the snub 35 at the proximal end 36 of the pin 33 may be modified to assure that the spring 49 will bear upon the snub 35 urging the snub towards the center of the barrel so that the surface 37 of the snub 35 will contact the inner face 32 of the plunger after it has passed by the snub and prevent the plunger from being withdrawn again.

FIG. 8 illustrates another embodiment in which the side wall 38 of the barrel 21, at the place of imbedding of the proximal end 36 of the pins 33, is thickened, as at 53 to provide an additional support for the proximal ends 36. The proximal ends 36 may be slightly modified by including a hook 54. The thickened portion 53 may encircle the barrel 21 and any process may be used to bind the pins within the thickened portion 53 and bind the thickened portion 53 to the barrel 21. A needle 46 has a rib receiving indent 48.

In the embodiment of FIG. 10 the guiding, proximal end cap 28 is modified to provide a quadri-partite female guide openings 71, 72, 73 and 74. The female guide openings receive a plunger having elongated male members 81, 82, 83, 84 which slide through said female guides into elongated guiding wings 85, 86, 87, 88 which extend axially within the barrel of cap 28. As the plunger is either retracted or fully extended, the guides prevent the plunger from being rotated and the pins broken off thereby preventing reuse of the syringe. The rod 24 is in this embodiment elongated in a cruciform cross-sectional shape. (see FIG. 9). The cruciform shape is complementary to the cruciform opening in the cap 28. The elongated guiding wings 85, 86, 87, and 88 at their distal ends 91, 92, 93 and 94 are modified to provide a quadri-partite guiding form.

Figure 11:
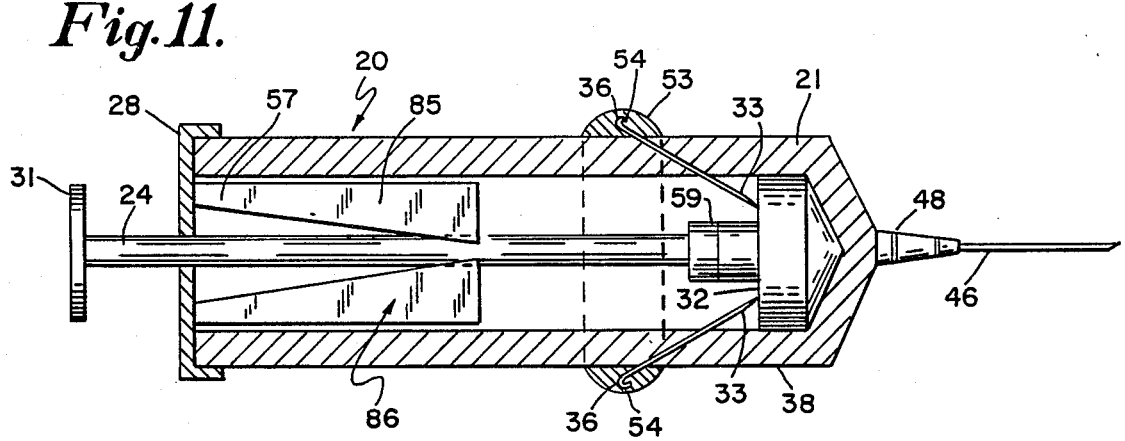
FIG. 11 is a view of the embodiment of FIG. 8 with the piston head in a different position and also showing a variation in construction.

The elongated wings 85, 86, 87 and 88 are narrowed as they approach the proximal ends 57 near the cap 28. The guiding wings 85, 86, 87 and 88 are sufficiently narrowed at their proximal ends 57 so that they may flex. The purpose of this arrangement is to allow head 59 at the distal end of the rod adjoining and joined to the plunger 22 to pass by the wings 85, 86, 87 and 88 and spread the broader distal ends 91–94 of the guiding wings 85–88. After the head 59 passes through the guiding wings, the joined plunger and head 59 may not return beyond the distal end of the guiding wings. This restricts the volume or dosage which may be administered by the syringe 20. At the same time with this modification, as with others, the plunger 22, after passing distally beyond the distal ends 34 of the pins 33 is prevented from returning toward the proximal end by the interposition of the distal ends 34 of the pins 33 as shown in FIG. 11. A tri-partite dimension (not illustrated) may also be employed, being also non-circular and symmetrical about the axis.

Figure 12:
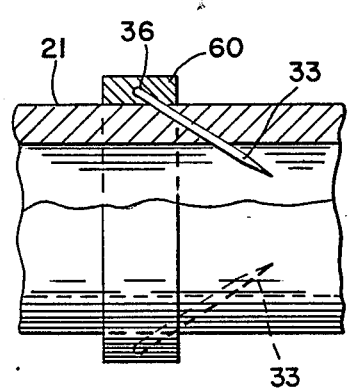
FIG. 12 is a partial view showing an alternative manner in which pins may be fastened in the barrel of the syringe.

FIG. 12 is a partial view which illustrates a different way in which the pins may be attached to the barrel 21. A ring 60 is slipped over the barrel and over the portion at which the proximal ends 36 of the pins 33 are to be sealed. Heat treatment of this portion then causes the sleeve to become sufficiently soft for penetration of the ends 36 of the pins to be imbedded within the ring 60 and the wall 38 of the barrel 21.

Figure 13:
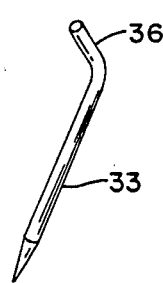
FIG. 13 is a perspective view of a different pin that may be employed in various embodiments.
Figure 14:
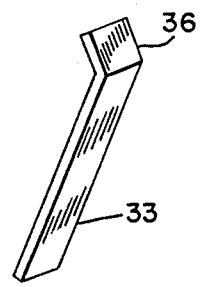
FIG. 14 is a perspective view of a different pin that may be employed in various embodiments.

The particular shape of the pins is not critical. For example the pin may preferably be of round cross-section, as indicated in the perspective view of FIG. 12 and 13, or of rectangular cross-section, as indicated in the perspective view of FIG. 14.

Figure 15:
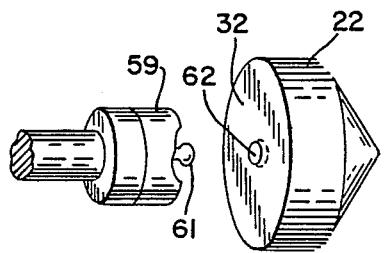
FIG. 15 illustrates a means of attaching an actuating rod to a plunger.

FIG. 15 illustrates a manner of attaching the head 59 to the plunger 22. The head 59 may have a nipple 61 centrally on its distal side which mates with a matching centrally located aperture 62 on the inner face 32 of the plunger 22. When the head 59 is pressed against the plunger face 32, the nipple 61 is forced into the mating aperture 62 and the enlarged plastic nipple head enters the enlargement of the aperture to attach the head 59 to the plunger 22. With this arrangement it is not possible to withdraw the head 59 against the force of the pins 33 because the head 59 will then pull the nipple 61 from its lodgment in the aperture 62, causing the parts to separate. Clearly a similar arrangement will be operative with any of the embodiments by supplying a head 59 with the nipple and the plunger with the mating aperture, or vice versa.

Preferably the syringe is constructed of a resin based material, for the various parts, except for the pins, which preferably are of stainless steel. The plunger 22, rod 24 in any of its forms, and the grip 31 may be of a suitable metal.

From the foregoing description it is apparent that there is described a syringe for one-time use for the administration of injections.

The invention as described is susceptible to various modifications, changes, and adaptations, and these are intended to be comprehended within the meaning and range of equivalents of the appended claims.

I claim:

1. A disposable syringe for one-time use comprising:
   a cylindrical barrel having a side wall, an axis, and two ends one of which is a distal end for the administration of a fluid;
   a cylindrical plunger mounted snugly and fluid tight for axial movement within the barrel;
   an actuating rod connected to the plunger and of radial extent less than that of the plunger, the barrel having at the other, proximal end means for guiding the actuating rod axially;
   a pin of spring material within the barrel and having two ends, the proximal end being securely fixed and sealed imbedded in the side wall at an axial position and the other, distal end being free and located axially within the barrel nearer the other, distal end of the barrel than the axial position of imbedment of the pin and having a position radially within the side wall;
   the plunger being movable by the actuating rod from a position nearer the one, distal barrel end to a position nearer the other, proximal barrel end and beyond the proximal end of the pin, the barrel on such movement camming the pin free end aside from its normal position toward the wall of the barrel until with continued plunger movement the free end is freed and returns by elasticity of the spring material to its normal position radially within the wall;
   whereby on such movement the plunger is captured by the pin at its free end to prevent return movement of the plunger toward the proximal end of the barrel and thereby to prevent re-use of the syringe.

2. A disposable syringe as claimed in claim 1, further comprising at least one other pin of spring material located within the barrel and each said pin having two ends, one, proximal end being securely fixed and sealed to the side wall at the same axial position as the first pin but at equal angular intervals about the axis, and the other, distal ends of the other pins being free and located axially at the same point as the distal end of the first pin.

3. A disposable syringe as claimed in claim 1, the said side wall possessing a buttressing support of greater diameter than the cylindrical portion to lend support for the said pin at the proximal position of the pin.

4. A disposable syringe as claimed in claim 1, the said syringe having a stroke in the axial direction toward the barrel distal end closer to the barrel distal end than the distal pin end.

5. A disposable syringe as claimed in claim 1, the said syringe having a stroke in the axial direction toward the distal barrel end beyond the position of the distal end of the pin.

6. A disposable syringe as claimed in claim 1, the pin having a head at the free, distal end facing the barrel, and the barrel having a pocket to receive the pin head during the camming action of the plunger.

7. A disposable syringe as claimed in claim 5, further comprising a compression spring contained within the pocket to assist the pin in moving towards its normal position radially within the side wall.

8. A disposable syringe as claimed in claim 2, further comprising a ring about the side wall at the position of the seal and itself sealed to the side wall to lend support to the said pins at the seal.

9. A disposable syringe as claimed in claim 1, the said pin being circular in cross-sectional shape.

10. A disposable syringe as claimed in claim 1, the said pin being rectangular in cross-sectional shape.

11. A disposable syringe as claimed in claim 1, the said guiding means comprising a head for the barrel having an opening, the said actuating rod having a cross-sectional shape complementary to said opening and closely fitting within it.

12. A disposable syringe as claimed in claim 11, the said guiding means opening being circular.

13. A disposable syringe as claimed in claim 11, the said guiding opening being non-circular.

14. A disposable syringe as claimed in claim 11, the said guiding means being tripartite, with three similar parts about the axis.

15. A disposable syringe as claimed in claim 11, the said guiding means being quadripartite, with four similar parts symmetrical about the axis.

16. A disposable syringe as claimed in claim 11, the said guiding means having axial extent and elasticity, the actuating rod camming the guiding means open as the rod moves toward the distal end, the actuating rod having a portion smaller in diametral extent about the axis at the distal end, whereby the guiding means, after a full stroke of the actuating rod and plunger, interferes by interposition to prevent a return stroke of the rod.

17. A disposable syringe as claimed in claim 1, the said barrel having an open groove to receive the pin throughout its length except for the imbedded end, whereby the length of the pin is smooth within the barrel as the plunger passes over the pin.

18. A syringe as claimed in claim 2, there being one other pin located diametrically opposite the first pin.

* * * * *